(12) United States Patent
Ginn et al.

(10) Patent No.: US 9,027,563 B2
(45) Date of Patent: May 12, 2015

(54) FALLOPIAN TUBE OCCLUSION DEVICES AND METHODS

(75) Inventors: Richard S. Ginn, Gilroy, CA (US);
David White, Sunnyvale, CA (US);
Ryan S. Christian, San Jose, CA (US);
Jeffrey J. Christian, Morgan Hill, CA (US)

(73) Assignee: Promed, Inc., Santa Clara, CA (US)

( * ) Notice: Subject to any disclaimer, the term of this patent is extended or adjusted under 35 U.S.C. 154(b) by 758 days.

(21) Appl. No.: 12/582,937

(22) Filed: Oct. 21, 2009

(65) Prior Publication Data

US 2010/0037900 A1 Feb. 18, 2010

Related U.S. Application Data

(62) Division of application No. 11/833,182, filed on Aug. 2, 2007, now Pat. No. 7,647,930.

(60) Provisional application No. 60/821,238, filed on Aug. 2, 2006.

(51) Int. Cl.
*A61F 6/06* (2006.01)
*A61F 6/22* (2006.01)

(52) U.S. Cl.
CPC ..................... *A61F 6/225* (2013.01)

(58) Field of Classification Search
CPC ............. A61F 6/225; A61F 6/06; A61F 6/20; A61F 6/22

USPC ........... 128/831, 830, 833; 424/432; 606/193, 606/191

See application file for complete search history.

(56) References Cited

U.S. PATENT DOCUMENTS

| | | | |
|---|---|---|---|
| 5,728,134 A | 3/1998 | Barak | |
| 6,695,867 B2 * | 2/2004 | Ginn et al. | 606/213 |
| 6,763,833 B1 | 7/2004 | Khera et al. | |
| 6,871,650 B1 | 3/2005 | Nikolchev et al. | |
| 7,220,259 B2 * | 5/2007 | Harrington et al. | 606/28 |
| 7,771,452 B2 * | 8/2010 | Pal et al. | 606/200 |
| 2005/0172972 A1 | 8/2005 | Nikolchev et al. | |
| 2009/0143815 A1 | 6/2009 | Eidenschink | |

OTHER PUBLICATIONS

Office Action dated Nov. 10, 2014, from corresponding JP application No. 2012-555194.

* cited by examiner

*Primary Examiner* — Victoria J Hicks
(74) *Attorney, Agent, or Firm* — Sheppard Mullin Richter & Hampton LLP

(57) ABSTRACT

A device for occluding body lumens such as fallopian tubes which has an occluder element which has a lumen and a fixation element located in the lumen of the occluder element. The fixation element has at least one looped wire which has a proximal region which is biased radially outwardly and be constrained prior to deployment of the device.

9 Claims, 8 Drawing Sheets

FALLOPIAN TUBE OCCLUSION DEVICES AND METHODS

CROSS-REFERENCE TO RELATED INFORMATION

The application claims priority to U.S. provisional patent application Ser. No. 60/821,238 filed on Aug. 2, 2006 and is a divisional of U.S. application Ser. No. 11/833,182 filed on Aug. 2, 2007 now U.S. Pat. No. 7,647,930, which are fully incorporated herein by reference.

BACKGROUND OF THE INVENTION

The present invention relates generally to contraception, and more particularly, to intrafallopian contraceptive devices and non-surgical methods for their delivery.

The art to which the present invention is directed is described in United States Published Patent Application No. 2005/0172972, the entirety of which is incorporated herein by reference.

SUMMARY OF THE INVENTION

One embodiment disclosed herein comprises a cap and a body. The body is provided with expandable attachment means which collapse when the device is placed under axial stress. When the stress is removed, the compressed attachment means expand. The device can be used to occlude the fallopian tube without perforating it. Another embodiment comprises at least one looped wire adapted to be deployed within a fallopian tube.

The device, and its deployment in this manner, achieve virtually instant sterilization.

DETAILED DESCRIPTION OF THE INVENTION

Figure 1:
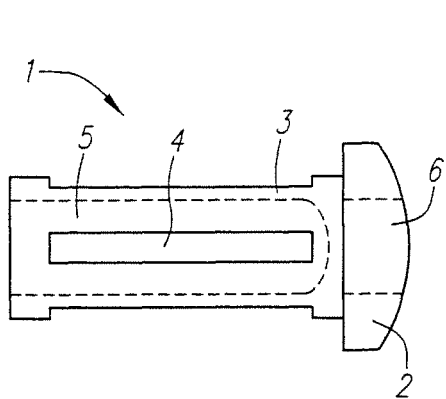
FIGS. 1 and 2 show the occluder without a delivery device with the body in the extended, stressed condition in FIG. 1 and in the unstressed shortened condition in FIG. 2.

As shown in FIG. 1, the occluder 1 comprises a cap 2, a body 3, attachment device 4 and plug 5. Cap 2 is provided with through hole 6. As shown, the body is in an extended, stressed condition and expansion means 4 is in a collapsed condition.

Figure 2:
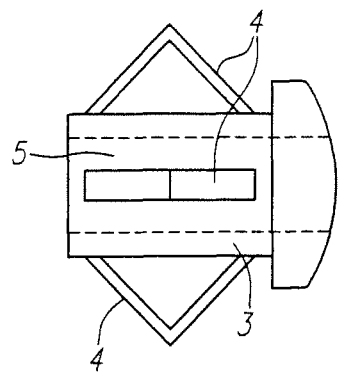

FIG. 2 shows occluder 1 with attachment means 4 in their expanded configuration after the lengthening stress on body 3 has been removed.

As can be seen in a comparison of FIG. 2 with FIG. 1, the lengthening of body 3 is accomplished by exerting axial force on plug 5. When that force is removed, plug 5 assumes its unstressed shorter configuration as shown in FIG. 2 and plug 5 moves into through hole 6 such that there is no longer an opening in cap 2. The body 3 may be made of nitinol metal while cap 2 and plug 5 may be made from a suitable polymer material.

Figure 3:
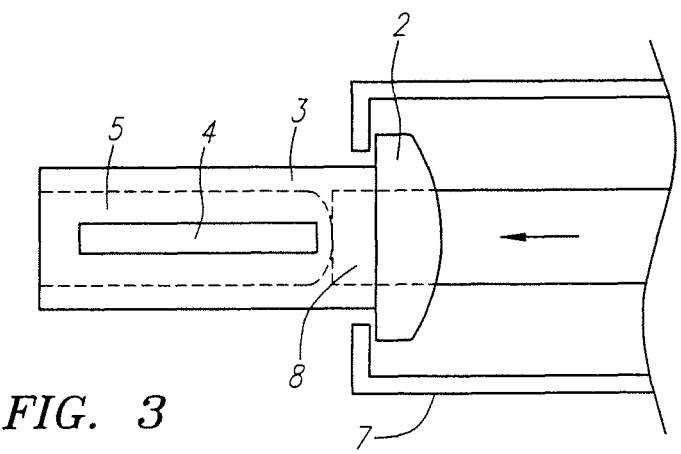
FIGS. 3 and 4 show the occluder device in combination with the deployment device, with the attachment means collapsed in FIG. 3 and expanded in FIG. 4.

FIG. 3 shows the occluder in combination with a delivery means comprising grasper 7 and plunger 8. In the configuration shown in FIG. 3, plunger 8 pushes on plug 5 to cause the body 3 to assume its extended, stressed configuration and causes grasper 7 to engage cap 2.

Figure 4:
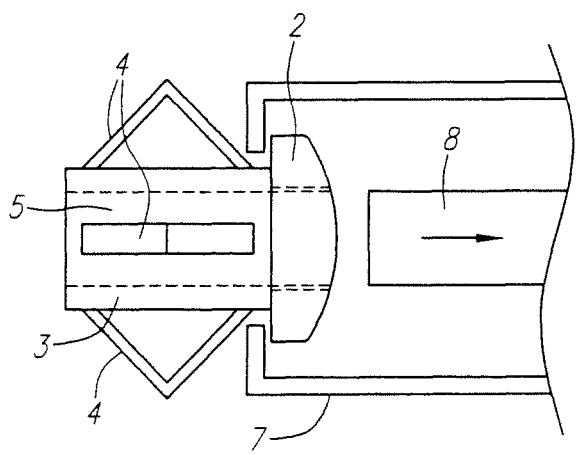

As shown in FIG. 4, when plunger 8 is retracted, body 3 shortens and attachment members 4 assume their expanded configuration. This shortening of body 3 moves plug 5 into the through hole 6 in cap 2.

Figure 5:
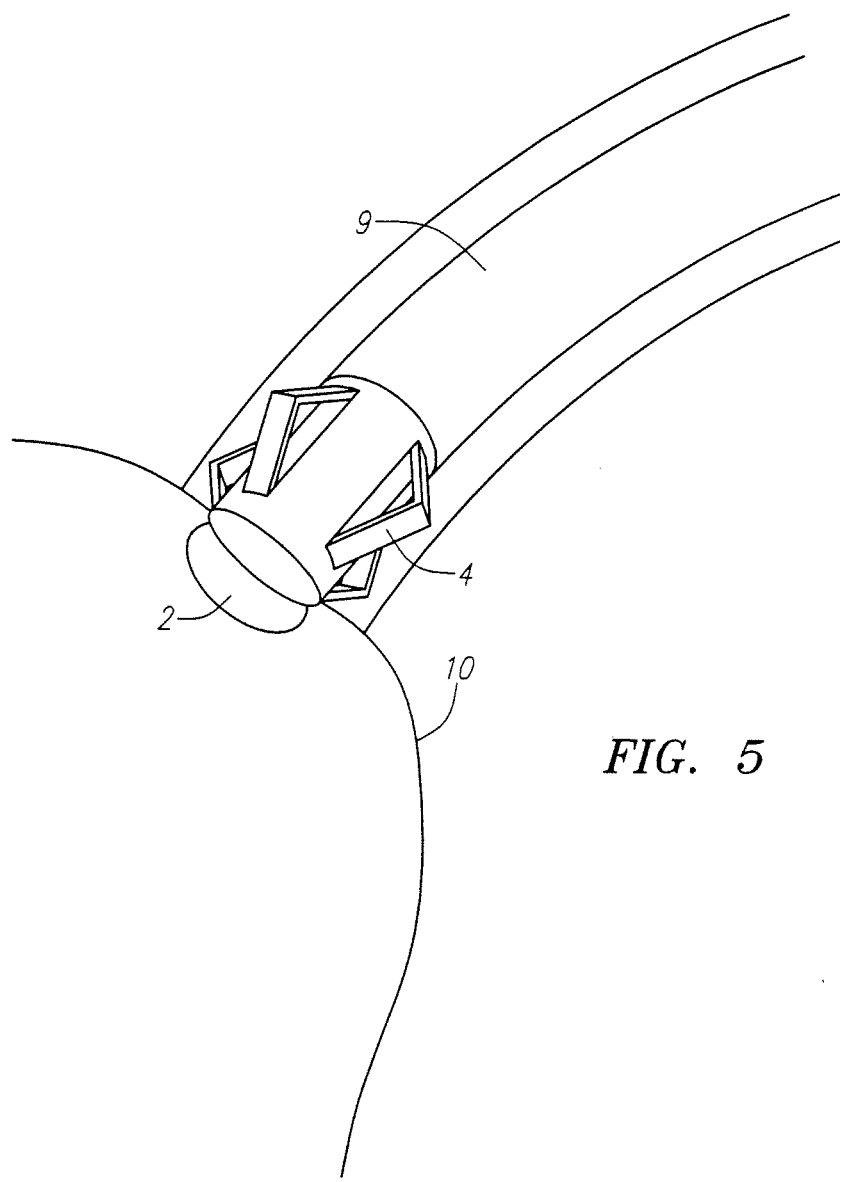
FIG. 5 shows the device after installation in the fallopian tube.

FIG. 5 shows the occluder device after installation with attachment means 4 engaging the wall of fallopian tube 9 and cap 2 sealing the fallopian tube at uterus wall 10. Once deployed, the device achieves virtually instant sterilization.

Figure 6:
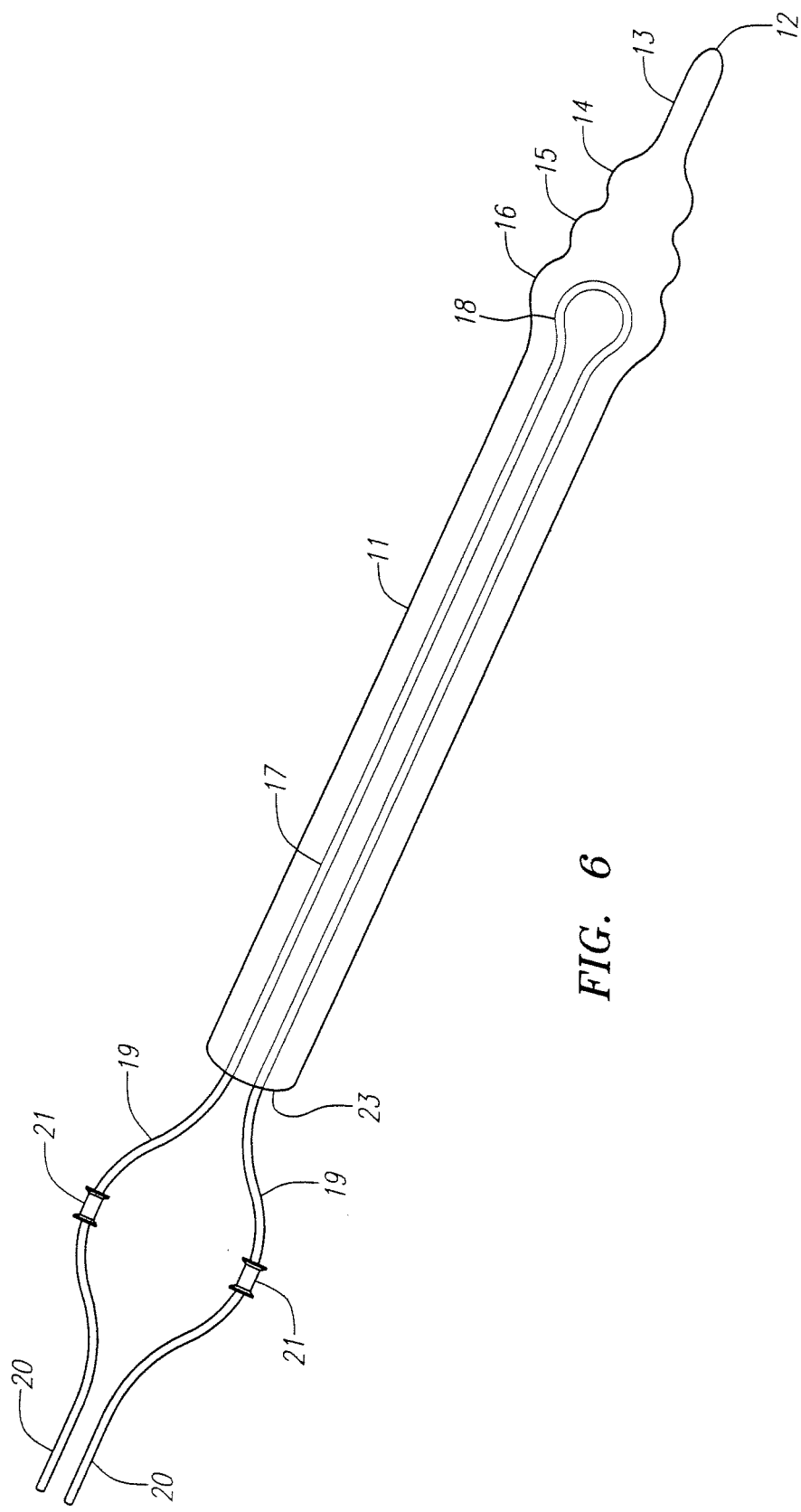
FIG. 6 shows an alternate embodiment of the occlusion device of the present invention which comprises an occluder element and a fixation element in which the fixation element comprises a looped wire.

An alternate embodiment of the occluder device of the present invention is shown in FIG. 6. In this embodiment, the occluder device has a distal portion which is the occluder element and a proximal portion which is the fixation element. The occluder element comprises a tubular portion 11 which is preferably fabricated from a soft polymeric or elastomeric material which has a distal end region 12 with a relatively narrow diameter. Located proximally to the distal region 12 are a series of spaced ribs 13-16 which have progressively increasing diameters. The portion of the occluder element extending from the narrow diameter tip to the largest diameter rib 16 may be hollow or solid. The number of ribs shown in FIG. 6 is exemplary only and there may be a lesser or greater number of ribs. Each of the ribs plays a role in occluding a fallopian tube, but the largest diameter rib is the primary occluding element. A fixation element 17 which has a distal portion 18 and a proximal portion 19 extends from a point proximal to the proximal end of the occlusion element 11 to a point in the region of the distal end of the occluding element, typically in the region of ridge 16. The distal end 18 of the fixation element may comprise an enlarged loop as shown in FIG. 6 or may have any other suitable configuration. A proximal portion 19 of the fixation element 17 preferably bows outwardly as shown in FIG. 6 with a straight portion 20 proximal to the bowed portion 19. As will be described in more detail below, the bowed portion 19 of the fixation element is fabricated from a resilient or elastic material which can be deformed such that it is in alignment with straight portions 20 when constrained by a sleeve (not shown) and which will revert to its bowed configuration when the constraint is removed as shown in FIG. 6. Optionally, a tissue-engaging element 21 can be attached to the bowed portions 19. For example, the fixation device may have the configuration of a flared cylinder as shown in FIG. 6 or it can have other configurations such as a barb, hook, or other projection including the type shown as element 4 in FIG. 2 hereof.

Figure 7:
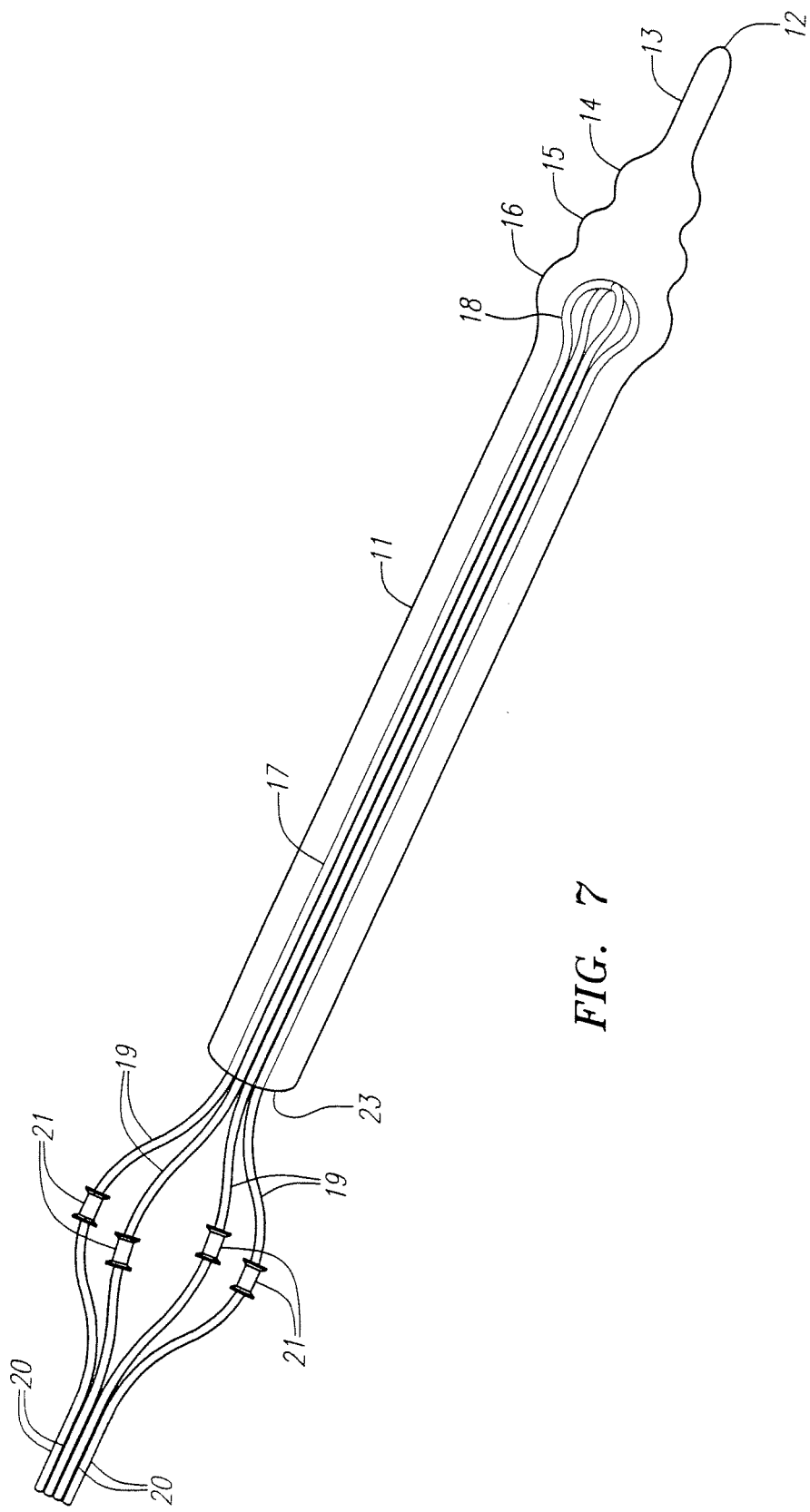
FIG. 7 shows a variation of the embodiment of FIG. 6 in which the fixation element comprises two looped wires.

FIG. 7 illustrates an occlusion device similar to that illustrated in FIG. 6 and the same reference numerals are used for the same elements. However, in FIG. 7, the illustrated embodiment has a fixation element comprising two looped wires rather than one looped wire as shown in FIG. 6.

Figure 8:
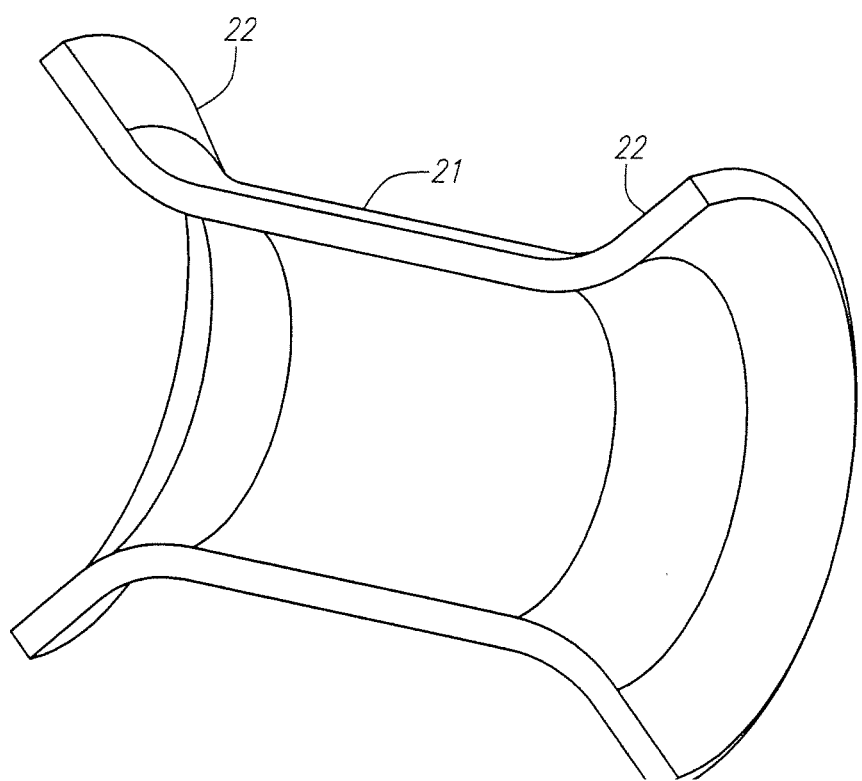
FIG. 8 shows a fixation enhancing attachment which may be added to the fixation element.

FIG. 8 is a cross-sectional view of fixation enhancing attachment 21 which has flared ends 22.

Deployment of the occlusion devices of FIGS. 6 and 7 is accomplished by using a delivery device comprising two sleeves, an inner sleeve or tube which abuts the proximal end of occlusion element 11 and which constrains the bowed portions 19 of fixation element 17 such that they are aligned with proximal portions 20. A second outer sleeve or tube is positioned over occlusion element 11 and over the inner sleeve such that the distal end of the outer sleeve abuts the largest diameter rib 16. The outer sleeve is attached to a handle and is flexible. Preferably, the occlusion device is deployed in conjunction with the use of a hysteroscope which permits visualization of the target fallopian tube and which has a separate lumen adapted for delivery of the occlusion device. Thus, by first visualizing the fallopian tube and then manipulating the handle attached to the outer tube of delivery device, the occlusion device can be inserted into the fallopian tube such that, preferably, the insertion is deep enough for the proximal end 20 of the fixation device to be located within the fallopian tube. The outer and inner tubes are then removed such that the outer tube no longer contacts the occlusion device and such that the bowed portions 19 of the fixation element 17 are free to bow outwardly into contact with the tissue of the fallopian tube. If the optional fixation elements 21 are used, they will also be brought into contact with the tissue of the fallopian tube.

As with the device shown in FIGS. 1-5, the occlusion device of FIGS. 6 and 7 will immediately occlude the fallopian tube such that the waiting time associated with other fallopian tube occluders before they are effective in occluding a fallopian tube is not required.

The fixation element 17 can be made out of any suitable resilient or elastic material which may be either metal or polymeric, e.g., metals such as nitinol, stainless steel, plastic, reinforced plastics or other suitable materials may be used. Among the polymeric materials which may be used are included polyimides, polyolefins, polycarbonates, polyesters, polyamides, polyurethanes, synthetic rubbers, etc. Similarly, the occlusion element can be made from a wide variety of materials. Preferably, this element is made from a relatively soft material which may be rubber, synthetic rubber, a foam material which may be fabricated from the polymers identified above or from other materials. The occlusion element may also be made from metal, but a non-metal material is preferred for most uses.

Furthermore, a material may be added to the outside of the occlusion element which will promote scarring, typically by physical irritation of the fallopian tube tissue or by other scarring mechanisms which may include chemical compounds, to further insure the integrity of the occlusion of the fallopian tube.

Shape-memory metals or polymers are preferred for fabricating the fixation element 17. These shape-memory materials may be composites, e.g., polymers which contain particulate or other additives, such as carbon particles or fibers, and may be combinations of metal and polymer, such as a coated metal. The shape memory may be temperature dependent, i.e., actuated by heating or other energy input, or may be mechanical in nature. Such materials are well known to those skilled in the art.

Figure 9:
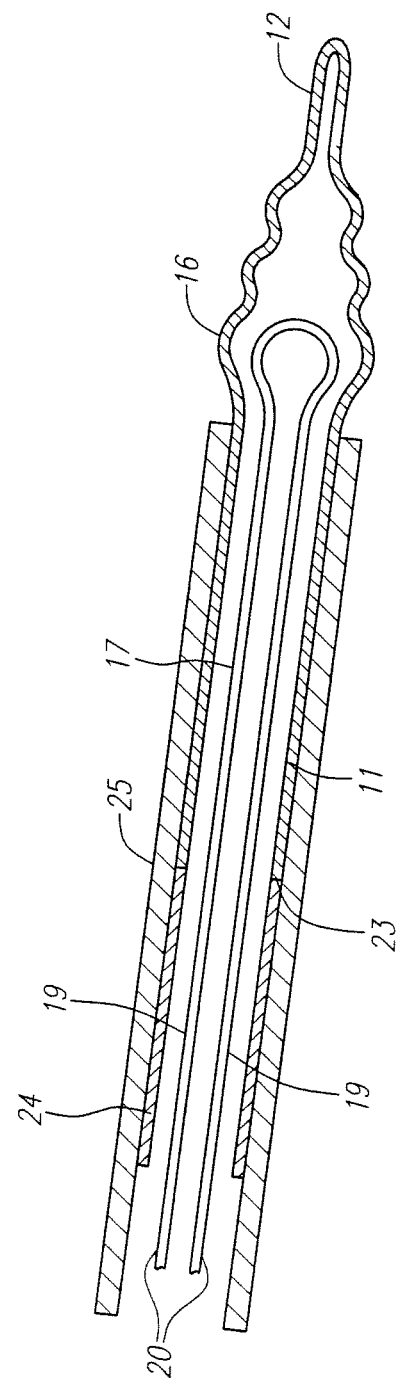
FIG. 9 is a schematic illustration of a portion of the deployment means used to deliver the occlusion device into the fallopian tube.

FIG. 9 is a schematic illustration of the delivery system of the present invention. As shown, inner tube 24 compresses the bowed portions 19 of the fixation element such that the bowed portions are aligned with the proximal portions 20. Outer sleeve 25 functions as a pusher element and is connected to a handle (not shown). The outer sleeve 25 is dimensioned so that it will fit in the additional lumen in a hysteroscope and, when pushed distally by applying force to the handle to which it is attached, will advance the occluding element into the fallopian tube. Once the desired location is achieved, outer sleeve 25 is removed. At this time, inner sleeve 24 which abuts the proximal end 23 of the occlusion element is also removed by pulling it in a proximal direction. When inner sleeve 24 is removed, bowed portion 19 of the fixation element will expand outwardly into the tissue of the fallopian tube to effectively hold the device in place.

Figure 10A:
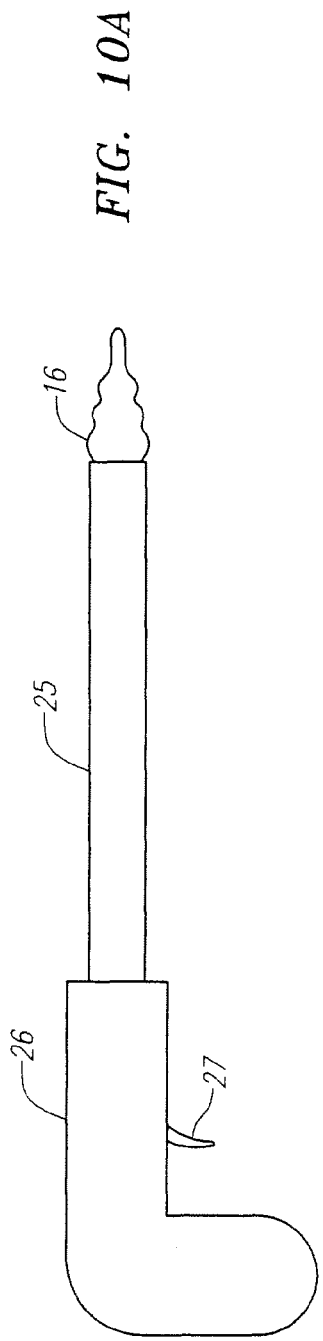
FIGS. 10A-C are sequential illustrations which show the several stages of deployment of the occlusion device.
Figure 10B:
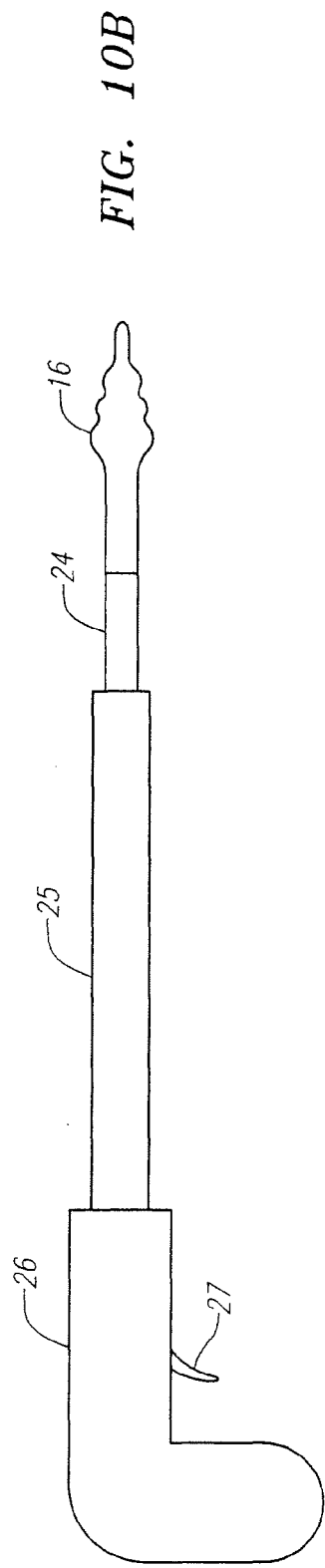
Figure 10C:
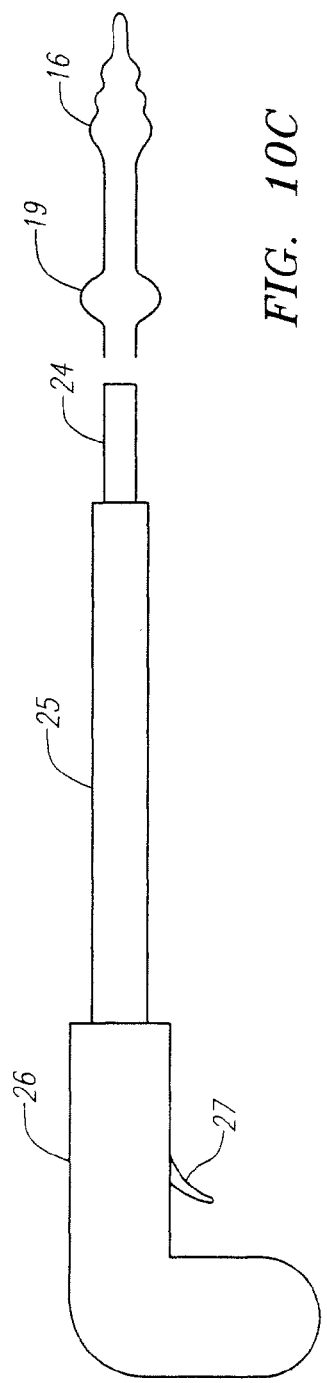

FIGS. 10A-C are sequential schematic drawings which further illustrate delivery of the occlusion device. In these drawings, element 26 is a handle which slidably receives outer sleeve 25. When trigger 27 is pulled, it slides outer sleeve 25 proximally away from the occlusion device to deploy it in the fallopian tube. Inner sleeve 24 is then also moved proximally to release bowed portions 19 of the fixation element as shown in FIG. 10C.

Figure 11:
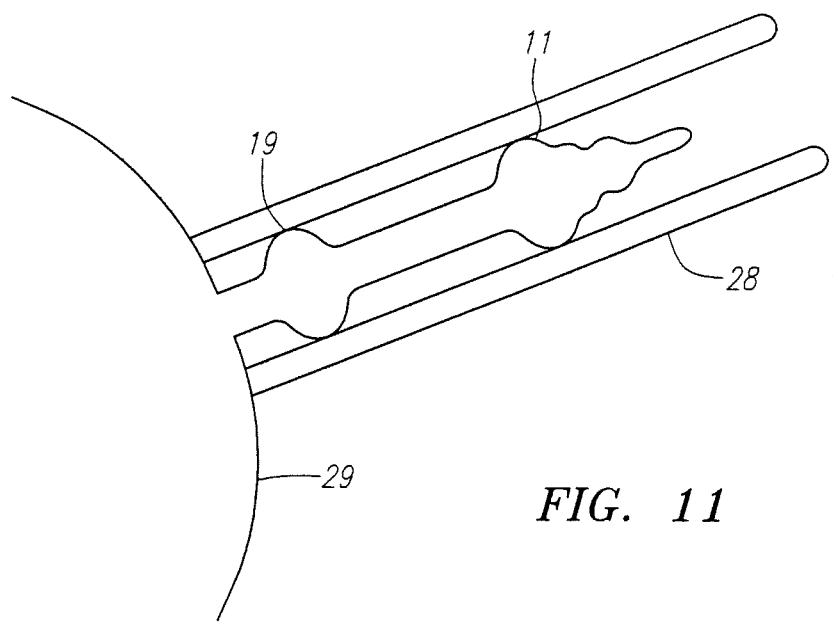
FIG. 11 is a schematic illustration which shows the occlusion device of FIG. 6 after it has been deployed in a fallopian tube.

FIG. 11 is a schematic illustration of the occlusion element 11 deployed in fallopian tube 28 with the bowed portion 19 of the fixation element engaged with the tissue of fallopian tube 28. In actual practice, the bowed portion 19 of the fixation element would penetrate the fallopian tube tissue and the occluder element would be large enough to cause the contour of the fallopian tube to be altered to be in a satisfactory degree of confirmation to the shape of the occluder device to assure effective occlusion.

The foregoing description of specific embodiments exemplifies the present invention and is but one embodiment thereof. Thus, it is to be understood that the scope of this invention is defined solely by the appended claims.

We claim:

1. A device for occluding a body lumen or passageway comprising an elongate member having a distal portion and a proximal portion,
    the distal portion of said member comprising an occluder element having a lumen and the proximal portion comprising a fixation element comprising at least one looped wire at its distal end,
    said at least one looped wire having two proximal wire portions in a proximal end region of the fixation element,
    said occluder element comprising an elongate tube having a distal end region having a narrower diameter than the diameter of the proximal end region, said distal end region comprising a plurality of spaced circumferential ribs,
    the proximal region of said fixation element extending proximally of the proximal end of said occluding element and the at least one looped wire at the distal end of said fixation element extending distally within the lumen of said occluding element to a location in the region of at least one of said ribs, and said fixation element being configured such that the proximal regions thereof have a portion which is biased radially outwardly but which can be constrained to be generally aligned with portions of the wires extending distally within the occluder element, said proximal region of said fixation element being adapted to fixedly engage tissue when in the unconstrained condition and to seal the body lumen.

2. The device of claim 1, wherein the occluder element is located in a delivery device which radially constrains the radially biased portion of the fixation element.

3. The device of claim 2, wherein the delivery device is provided with a pusher to move the occluder element distally out of the delivery device.

4. The device of claim 1, wherein said proximal region of said fixation element is provided with a fixation enhancement member.

5. The device of claim 1, wherein the outer surface of the occluder element is provided with a scar-promoting material.

6. The device of claim 1, wherein said fixation element comprises a plurality of looped wires.

7. The device of claim 1, wherein said occluder element comprises a polymer.

8. The device of claim 1, wherein the occluder element has a closed distal end.

9. The device of claim 1, wherein the occluder element has an open proximal end.

* * * * *